US010034783B1

(12) United States Patent
Highsmith et al.

(10) Patent No.: US 10,034,783 B1
(45) Date of Patent: Jul. 31, 2018

(54) ADJUSTABLE PROSTHETIC ANKLES

(71) Applicants: Michael Jason Highsmith, Tampa, FL (US); Derek James Lura, Fort Myers, FL (US)

(72) Inventors: Michael Jason Highsmith, Tampa, FL (US); Derek James Lura, Fort Myers, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 15/208,273

(22) Filed: Jul. 12, 2016

Related U.S. Application Data

(62) Division of application No. 14/574,083, filed on Dec. 17, 2014.

(60) Provisional application No. 61/917,033, filed on Dec. 17, 2013.

(51) Int. Cl.
*A61F 2/68* (2006.01)
*A61F 2/66* (2006.01)
*A61F 2/50* (2006.01)
*A61F 2/76* (2006.01)

(52) U.S. Cl.
CPC ............ *A61F 2/6607* (2013.01); *A61F 2/76* (2013.01); *A61F 2002/5018* (2013.01); *A61F 2002/5043* (2013.01); *A61F 2002/6614* (2013.01); *A61F 2002/6836* (2013.01); *A61F 2002/6854* (2013.01)

(58) Field of Classification Search
CPC .................. E05B 71/00; E05B 65/003; A61F 2005/0158; A61F 3/00; A61F 2/54; A61F 2/585; A61F 2/66; A61F 2/6602; A61F 2/6607; A61F 2002/5016; A61F 2002/5018; A61F 2002/502; A61F 2002/5021; A61F 2002/5023; A61F 2002/5083; A61F 2002/5084; A61F 2002/509; A61F 2002/6854
See application file for complete search history.

(56) References Cited

U.S. PATENT DOCUMENTS

| | | | | |
|---|---|---|---|---|
| 4,502,472 A | * | 3/1985 | Pansiera | A61F 5/0125 602/16 |
| 5,219,365 A | * | 6/1993 | Sabolich | A61F 2/66 623/53 |
| 5,800,564 A | * | 9/1998 | Gelineau | A61F 2/6607 623/38 |

(Continued)

OTHER PUBLICATIONS

Fradet, et al., Biomechanical analysis of ramp ambulation of transtibial amputees with an adaptive ankle foot system; Gait Posture 32(2): 191-198; 2010.

(Continued)

*Primary Examiner* — Thomas J Sweet
*Assistant Examiner* — Christie Bahena
(74) *Attorney, Agent, or Firm* — Thomas | Horstemeyer, LLP

(57) ABSTRACT

In one embodiment, an adjustable prosthetic ankle separate from a prosthetic foot includes an upper coupling member, a lower coupling member that couples with the upper coupling member, and a flexion angle adjustment mechanism associated with the coupling members that enables a user to change a relative angle between the coupling members, and therefore a flexion angle of the prosthetic ankle, without using any tools.

14 Claims, 8 Drawing Sheets

(56) References Cited

U.S. PATENT DOCUMENTS

| | | | | |
|---|---|---|---|---|
| 5,913,901 A | * | 6/1999 | Lacroix | A61F 2/66 623/47 |
| 6,217,249 B1 | * | 4/2001 | Merlo | F16C 11/0604 403/128 |
| 6,402,790 B1 | * | 6/2002 | Celebi | A61F 2/601 623/38 |
| 2005/0119763 A1 | * | 6/2005 | Christensen | A61F 2/6607 623/24 |
| 2007/0260328 A1 | * | 11/2007 | Bertels | A61F 2/585 623/38 |

OTHER PUBLICATIONS

Hansen, et al., Roll-Over characteristics of human walking on inclined surfaces; Hum. Mov. Sci. 23(6): 807-821; 2004.

Highsmith, et al., Ramp descent performance with the C-Leg and interrater reliability of the Hill Assessment Index; Prosthet. Orthot. Int. 37(5); 362-368; 2013.

Highsmith, et al., Spatiotemporal parameters and step activity of a specialized stepping pattern used by a transtibial amputee during a Denali mountaineering expedition. J. Prosthet. Orthot. 24(3): 153-157; 2012.

U.S. Dept. of Justice; ADA Standards for Accessible Design, Washington, DC; US Dept. of Justice; 2010.

Wolf, et al., Pressure characteristics at the stump/socket interface in transtibial amputees using an adaptive prosthetic foot. Clin. Biomech; 24(10):860-865; 2009.

www.ossur.com; ElationTM.

www.freedom-innovations.com; RunwayR HX.

\* cited by examiner

ADJUSTABLE PROSTHETIC ANKLES

CROSS-REFERENCE TO RELATED APPLICATION

This application is a divisional application of co-pending U.S. Non-Provisional Application entitled "Adjustable Prosthetic Ankles," having Ser. No. 14/574,083 and filed Dec. 17, 2014, and claims priority to U.S. Provisional Application Ser. No. 61/917,033 and filed Dec. 17, 2013, both of which are hereby incorporated by reference herein in their entireties.

BACKGROUND

Passive ankle prostheses generally do not enable large adjustments to ankle flexion angles. Although there are prosthetic ankles that enable variation of plantar flexion to accommodate heeled shoes, they are not designed for use with large angles of dorsiflexion for hill ascent. Studies have been conducted to investigate the path of the center of pressure relative to the shank, called the roll-over shape, of able-bodied individuals ascending and descending 0°, 5°, and 10° ramps. It was determined that the best fitting rotation of level ground roll-over shape corresponded with the angle of incline of the ramp for positive inclines of the ankle-foot roll-over shape and for positive and negative inclines of the knee-ankle-foot roll-over shape. Therefore, it is important to be able to accommodate the sagittal angle of the ankle to approximate the ground slope.

Prosthesis wearers routinely encounter sloped terrain in daily life. For instance, driveways are commonly sloped, as are wheelchair-accessible ramps used to access buildings and homes. In the U.S., the Americans with Disabilities Act of 1990 (ADA) provides regulations with respect to slopes to determine what is compliant. For instance, building access ramps should be approximately 5° to be considered in compliance for new construction. Specialized activities, such as construction work, military service, and emergency response, may require ambulation on steeply sloped terrain in a loaded condition. Traditional prosthetic ankles may be inadequate to sustain such terrain, as they are typically designed and tested for walking on level ground, stairs, or slight inclines. Mountaineering, which may be occupational or recreational, may require ambulation on extreme slopes under heavily loaded conditions.

In view of the above discussion, it can be appreciated that it would be desirable to have a prosthetic ankle that enables the user to adjust the flexion angle of the ankle to accommodate inclines and declines.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a prosthetic ankle that enables the user (e.g., wearer) to adjust the flexion angle of the ankle to accommodate inclines and declines, as well as various footwear, such as heeled shoes and boots. Disclosed herein are adjustable prosthetic ankles that are well-suited for such use. In some embodiments, the adjustable prosthetic ankles are independent (modular) components that can be used in conjunction with separate pylons and prosthetic feet. The ankles include flexion angle adjustment mechanisms that enable the user to quickly and easily change the flexion angle of the ankle without using any tools. In some embodiments, the flexion angle is infinitely adjustable. In other embodiments, the ankle is incrementally adjustable.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
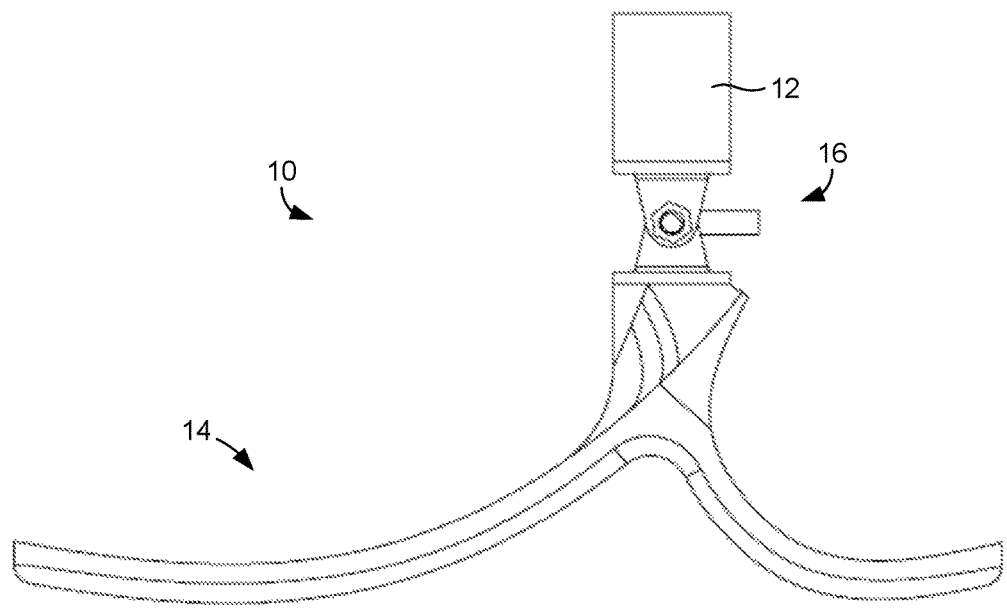
FIG. 1 is a side view of an embodiment of a lower-leg prosthesis that incorporates an adjustable prosthetic ankle.
Figure 2:
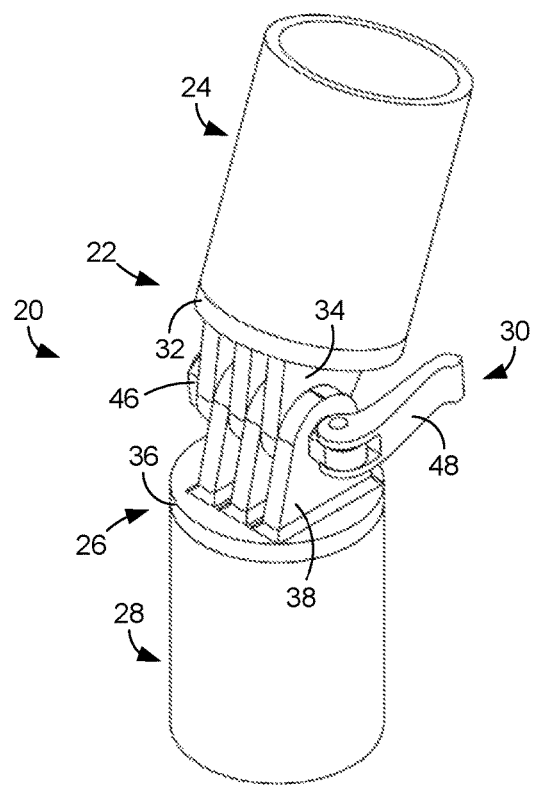
FIG. 2 is a perspective side view of a first embodiment of an adjustable prosthetic ankle that can be used in a lower-leg prosthesis, such as that of FIG. 1.

FIG. 1 is a side view of an embodiment of a lower-leg prosthesis 10 that incorporates an adjustable prosthetic ankle. As shown in the figure, the prosthesis 10 generally includes a shank or pylon 12 that replaces the wearer's missing shin, a prosthetic foot 14 that replaces the wearer's missing foot, and an adjustable prosthetic ankle 16 that connects the pylon and the foot.

FIGS. 2-5 illustrate a first embodiment of an adjustable prosthetic ankle 20 that can be used in a lower-leg prosthesis, such as one similar to that shown in FIG. 1. With specific reference to FIGS. 2 and 3, the ankle 20 generally comprises a first or upper coupling member 22 that is mounted to a first or upper shaft 24, a second or lower coupling member 26 that is mounted to a second or lower shaft 28, and a flexion angle adjustment mechanism in the form of a quick-release fastener 30 that connects the upper and lower coupling members together. The upper shaft 24 can either be part of the pylon of the lower-leg prosthesis or a component that connects the ankle 10 to the pylon. In similar manner, the lower shaft 26 can either be part of the prosthetic foot of the lower-leg prosthesis or a component that connects the ankle 10 to the prosthetic foot.

Figure 3:
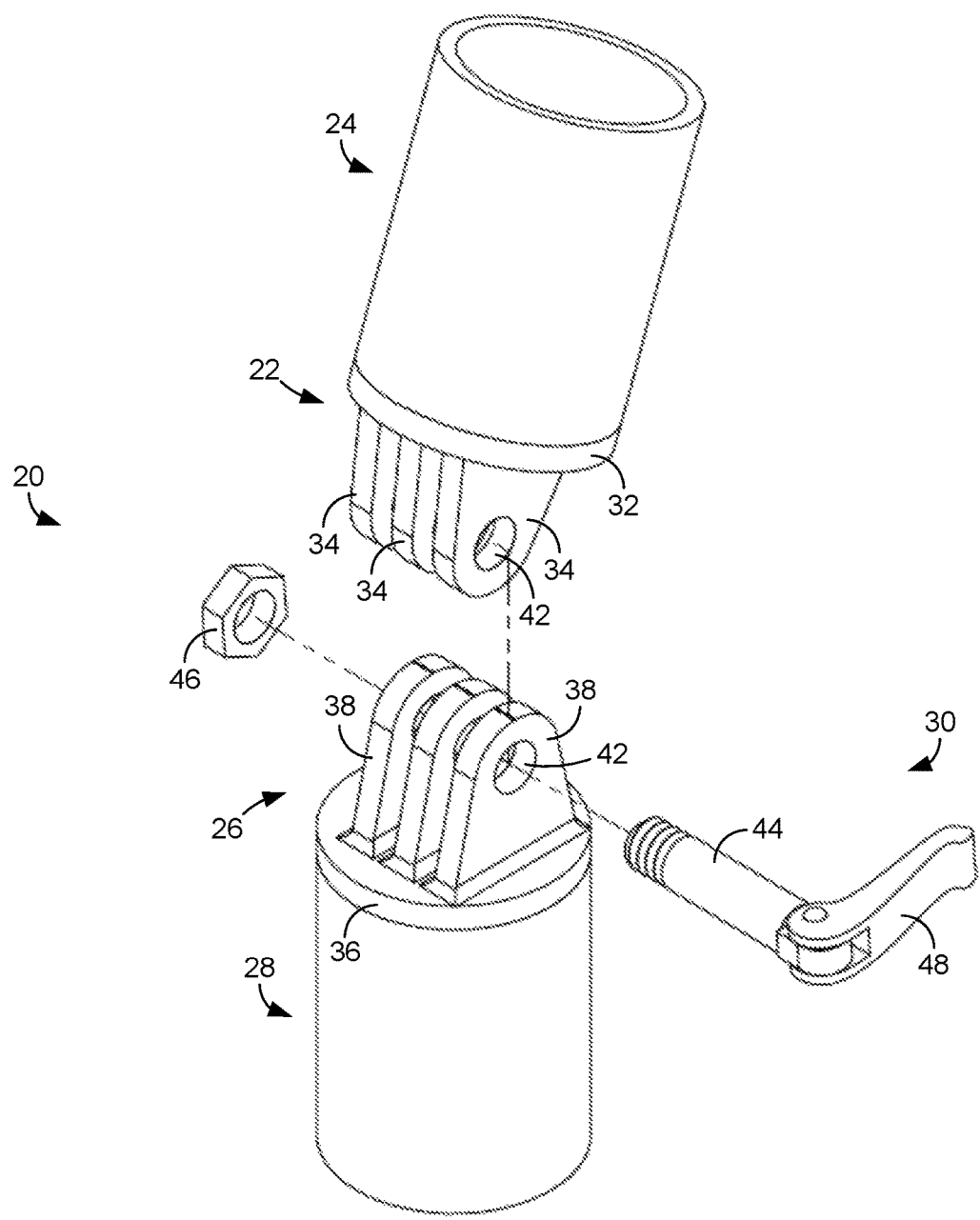
FIG. 3 is an exploded perspective side view of the adjustable prosthetic ankle of FIG. 2.

The upper and lower coupling members 22, 26 can be made of a strong metal material, such as a metal material like steel, aluminum, titanium, or alloys thereof, a composite material like carbon fiber, or a hard rubber material, and, as shown most clearly in FIG. 3, can have similar configurations. In the illustrated embodiment, the upper coupling member 22 includes a base 32 from which multiple parallel mounting flanges 34 downwardly extend, and the lower coupling member 26 includes a base 36 from which multiple parallel mounting flanges 38 upwardly extend. Each base 32, 36 can comprise a generally disc-shaped element that is adapted to connect with its associated shaft 24, 28. In some embodiments, the base 32, 36 can comprise a component (not shown) that extends into its associated shaft 24, 28 for purposes of securing it thereto.

Figure 4A:
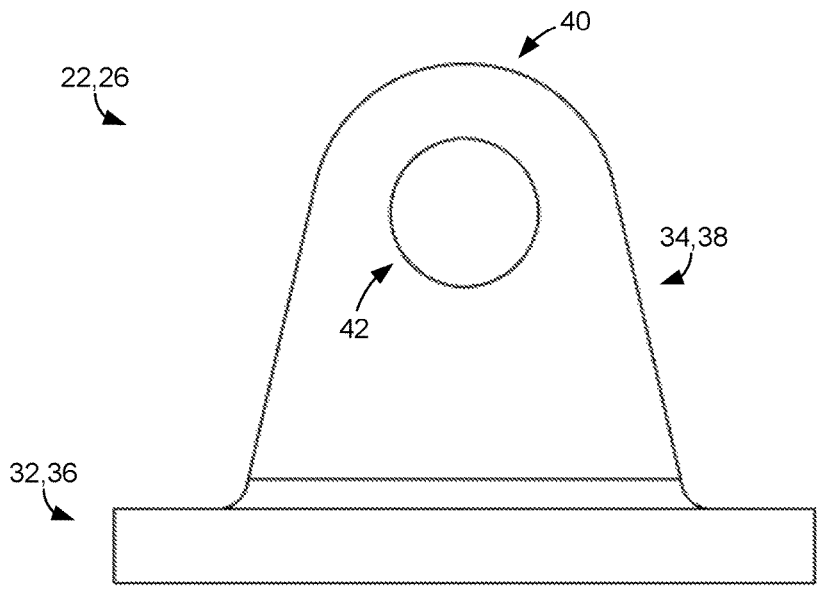
FIG. 4A is a first side view of a coupling member of the adjustable prosthetic ankle of FIGS. 2 and 3.
Figure 4B:
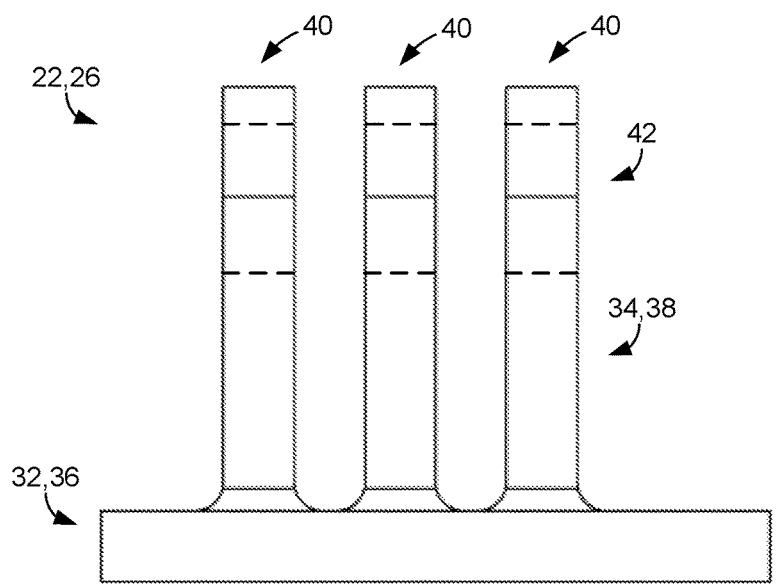
FIG. 4B is a second side view of the coupling member of FIG. 4A.

In the illustrated embodiment, each mounting flange 34, 38 is a planar element that extends from its associated base 34, 36 and tapers as it does so. As is apparent from FIG. 4A, each mounting flange 34, 38 can have a generally triangular shape that terminates in a rounded distal end 40. As is shown in FIG. 4A, each mounting flange 34, 38 has an opening 42 that is adapted to enable a bolt of the quick-release fastener 30 to pass.

With reference back to FIG. 3, the quick-release fastener 30 generally comprises a threaded bolt 44 that is adapted to pass through the openings 42 of the mounting flanges 22, 26. More particularly, when the mounting flanges 22, 26 are positioned so that they interleave with each other and their openings 42 align, the bolt 44 can be passed through each mounting flange and the bolt's distal end can be threaded into a threaded nut 46 positioned on the opposite side of the ankle 20.

Figure 5A:
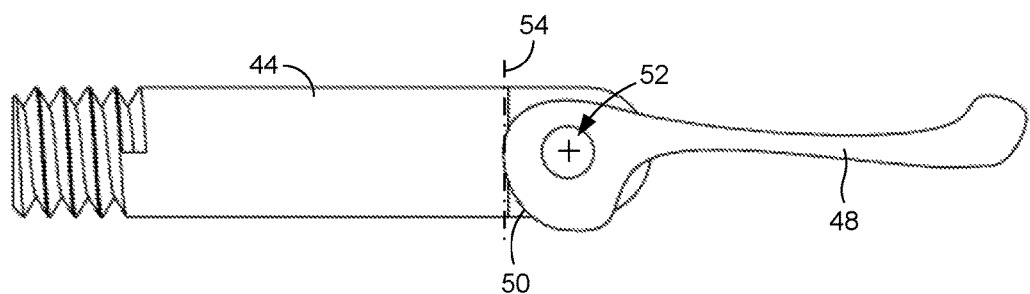
FIG. 5A is a side view of a quick-release fastener of the adjustable prosthetic ankle of FIGS. 2 and 3 shown in a released position.
Figure 5B:
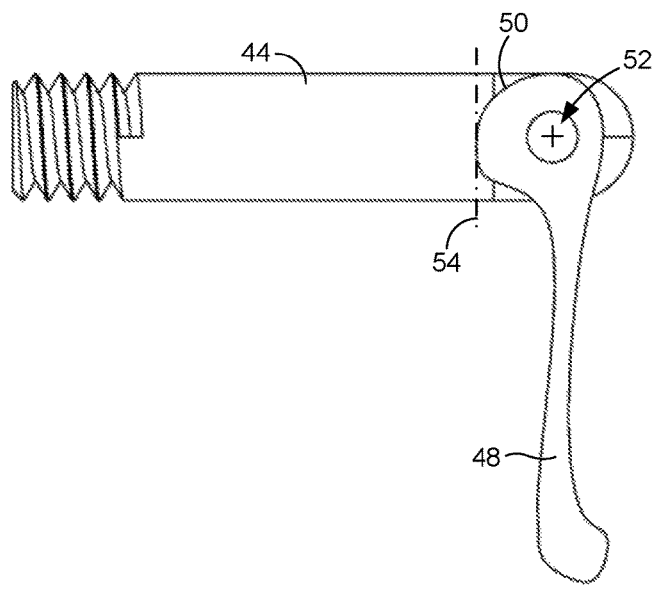
FIG. 5B is a side view of the quick-release fastener of FIG. 5A shown in a locked position.

An elongated lever 48 is pivotally mounted to the proximal end of the bolt 44 that can be used to lock and release the quick-release fastener 30. As shown most clearly in FIGS. 5A and 5B, the lever 48 comprises a curved, variable radius cam surface 50 that is adapted to engage the nearest mounting flange, which is represented by the plane 54. The lever 48 can be manually pivoted by the user about its pivot axis 52, which is proximate to the cam surface 50. As shown in FIG. 5A, when the lever 48 is flipped outward away from the plane 54 so as to place it in a released position, the distance between the pivot axis 52 and the portion of the cam surface 50 that engages the flange is relatively small. As shown in FIG. 5B, however, when the lever 48 is flipped inward toward the plane 54 so as to place it in a locked position, the distance between the pivot axis 52 and the portion of the cam surface 50 that engages the flange is relatively large. If the nut 46 is tightened to the extent that both it and the cam surface 50 firmly contacts a mounting flange 34, 38 when the lever 48 is in the released position of FIG. 5A, moving the lever to the locked position of FIG. 5B pinches the mounting flanges together so as to prevent relative angular motion of the upper and lower coupling members 22, 26 and, therefore, alteration of the flexion angle of the ankle 10.

During use of the prosthetic ankle 20, the lever 48 of the quick-release fastener 30 can be flipped outward, as illustrated by FIG. 5A, to enable the user to adjust the flexion of the ankle, and therefore the prosthetic foot, to a desired angle, whether it be in the dorsiflexion or the plantar flexion direction. Because of the nature of the coupling between the upper and lower coupling members 22, 26, infinite adjustment of the flexion angle is possible between its two extreme positions. Once the desired angle has been achieved, the user can simply flip the lever 48 inward, as illustrated by FIG. 5B, to lock the ankle 20 and prevent further angular movement between the upper and lower coupling members 22, 26. With such operation, the user can quickly and easily adjust the prosthetic ankle 20 and foot to the exact desired position. If desired, the resistance to motion of the ankle 20 can be adjusted by changing the torque placed on the nut 46, changing the number of flanges 34, 38 used, or modifying the material or surface properties of the flanges.

Figure 6:
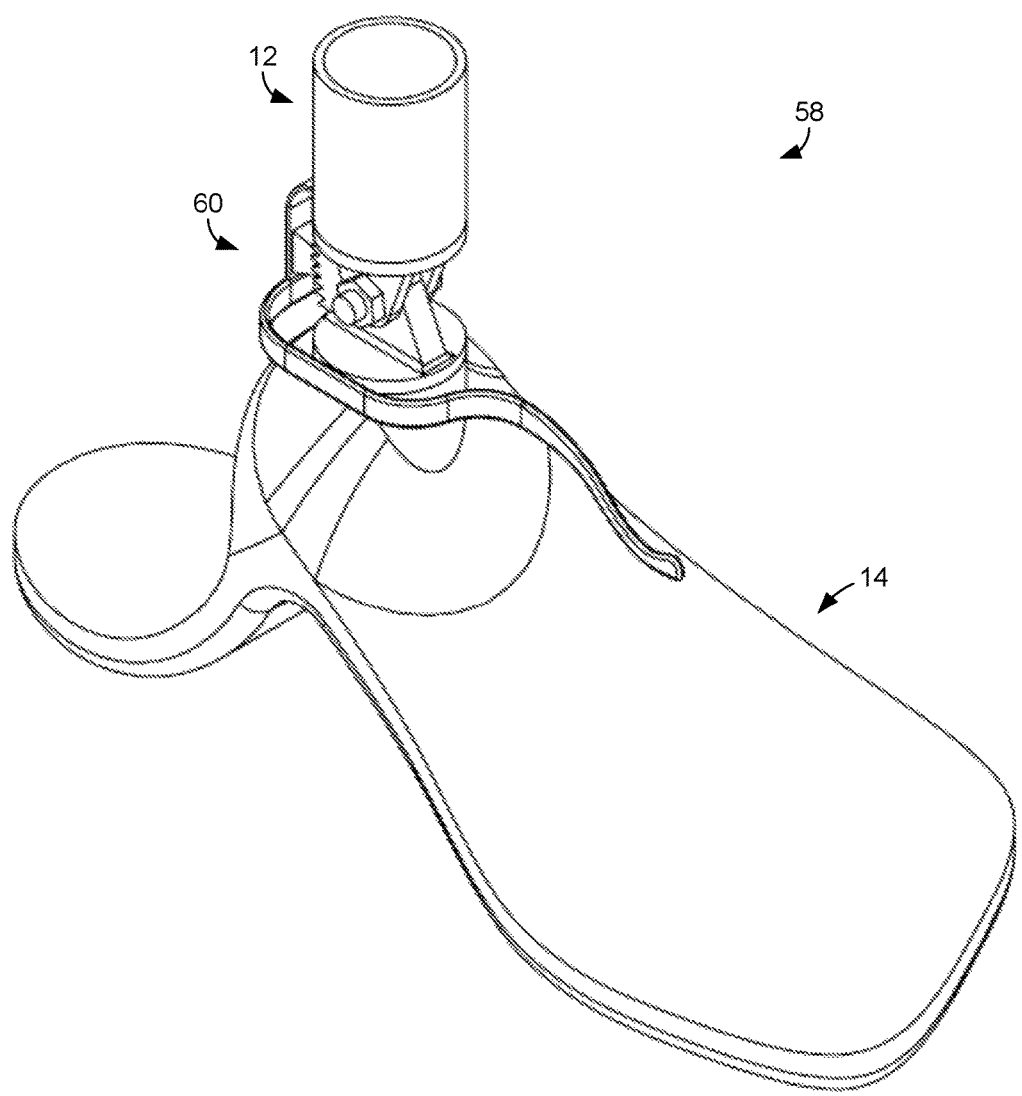
FIG. 6 is a perspective side view of a second embodiment of lower-leg prosthesis that incorporates an adjustable prosthetic ankle.
Figure 7:
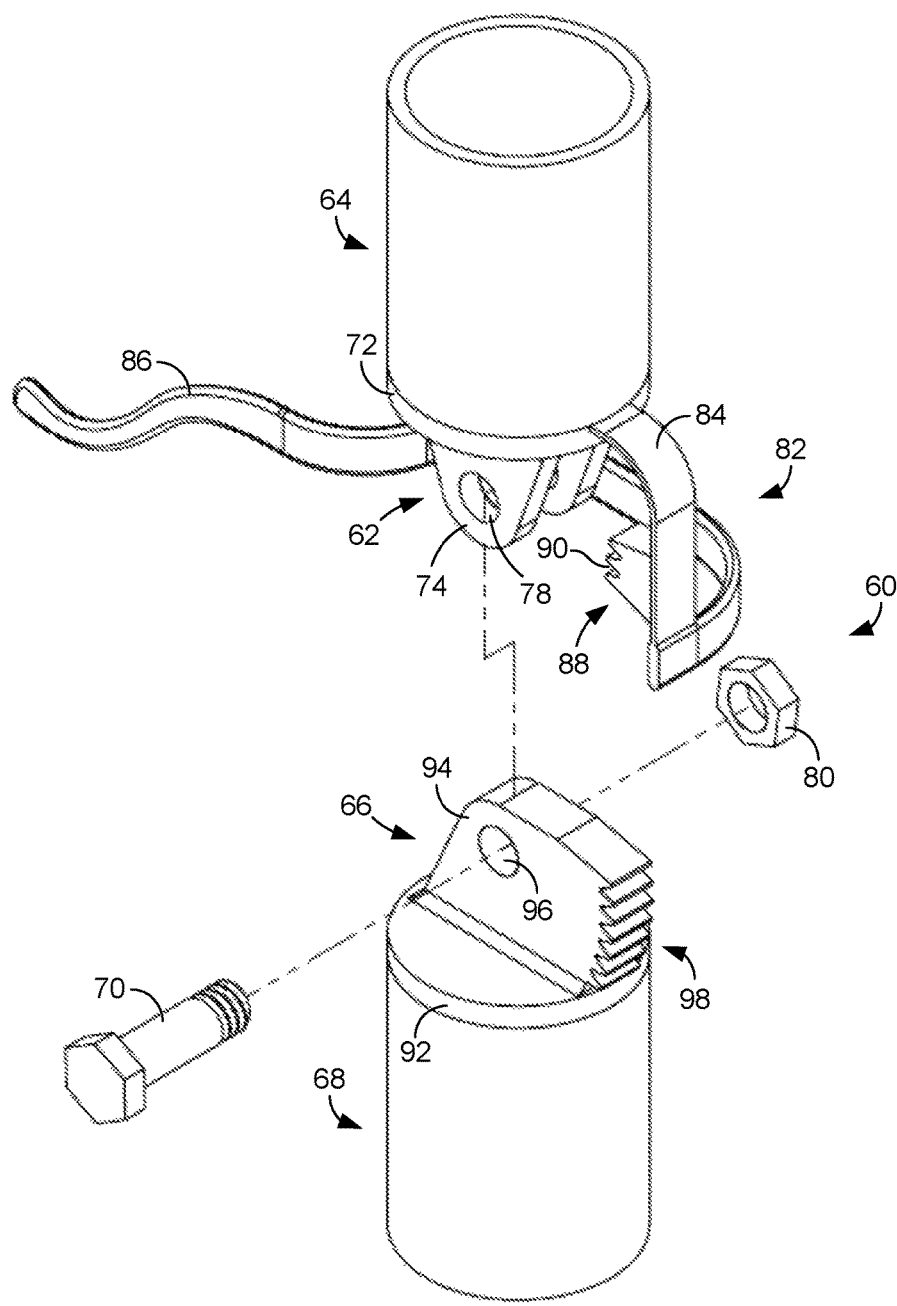
FIG. 7 is an exploded perspective side view of the adjustable prosthetic ankle shown in FIG. 6.

FIG. 6 illustrates an embodiment of a lower-leg prosthesis 58 that includes an alternative adjustable prosthetic ankle 60. With reference to FIG. 7, the ankle 60 generally comprises a first or upper coupling member 62 that is mounted to a first or upper shaft 64, a second or lower coupling member 66 that is mounted to a second or lower shaft 68, and a threaded fastener 70 that connects the upper and lower coupling members together. The upper shaft 64 can either be part of the pylon of the lower-leg prosthesis or a component that connects the ankle 60 to the pylon. In a similar manner, the lower shaft 66 can either be part of the prosthetic foot of the lower-leg prosthesis or a component that connects the ankle 60 to the prosthetic foot.

Figure 8A:
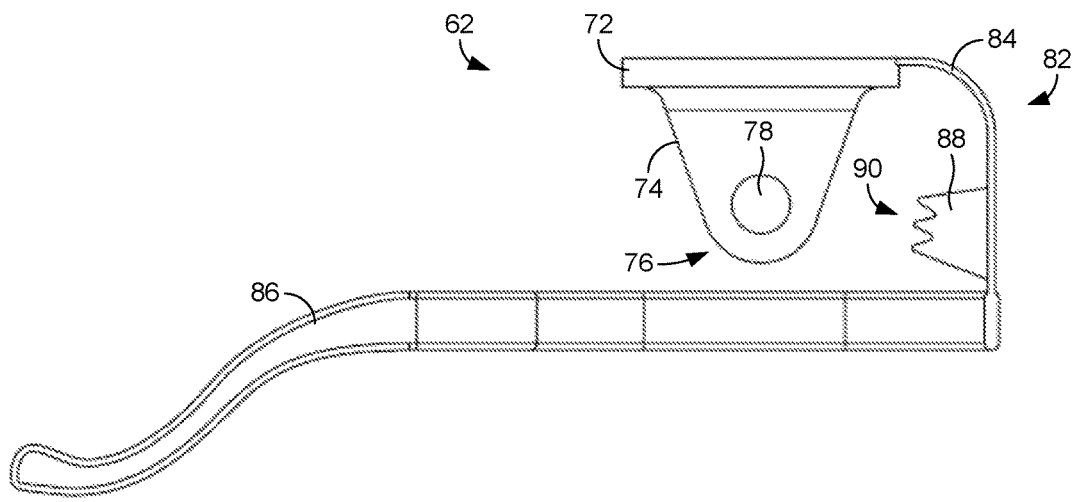
FIG. 8A is a side view of an upper coupling member of the adjustable prosthetic ankle of FIG. 7.

The upper and lower coupling members 62, 66 can be made of a strong material, such as a metal, composite, or hard rubber material. As is apparent from FIG. 7, the upper coupling member 62 includes a base 72 from which two parallel mounting flanges 74 downwardly extend. The base 72 can comprise a generally disc-shaped element that is adapted to connect with its associated shaft 64. In some embodiments, the base 72 can comprise a component (not shown) that extends into its associated shaft 64 for purposes of fixing it thereto. In some embodiments, the mounting flanges 74 have configurations similar to those described above for the mounting flanges 34, 38. Accordingly, as shown in FIG. 8A, the mounting flanges 74 can each comprise a planar element that extends from the base 72 and tapers as it does so. The mounting flanges 74 can have a generally triangular shape that terminates in a rounded distal end 76. In addition, each mounting flange 74 includes an opening 78 that is adapted to receive the threaded fastener 70. This fastener 70 can comprise a threaded bolt, which is adapted to thread into a threaded nut 80 (see FIG. 7).

As shown in FIGS. 7 and 8A, an adjustment lever 82, which forms a first part of a flexion angle adjustment mechanism, is connected to the base 72. In the illustrated embodiment, the lever 82 comprises a compliant element 84 that extends downward from the base 72 and an elongated lever arm 86 that extends forward from a distal end of the compliant element. As described below, the angle of the prosthetic ankle 60 can be adjusted when the user manipulates the lever arm 86 so as to bend the compliant element 84 outward. Extending inward from the compliant element 84 toward the center of the ankle 60 is a tooth block 88 that comprises inwardly facing teeth 90 that, as described below, are adapted to engage similar teeth provided on the lower coupling member 66.

Figure 8B:
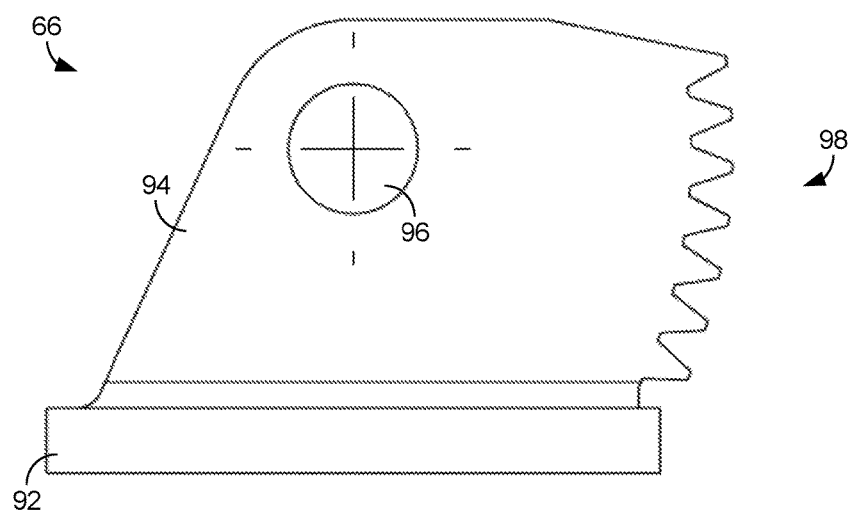
FIG. 8B is a side view of a lower coupling member of the adjustable prosthetic ankle of FIG. 7.

Referring next to FIGS. 7 and 8B, the lower coupling member 66 comprises a base 92 from which upwardly extends a mounting flange 94 that is sized and configured to fit between the mounting flanges 74 of the upper coupling member 62. As shown in FIG. 8B, the mounting flange 94 includes an opening 96 that is adapted to receive the threaded fastener 70. In addition, the mounting flange 94 includes a row of outwardly facing teeth 98 that are provided along a lateral edge of the flange. The teeth 98 are adapted to engage the teeth 90 of the lever 82 and therefore form a second part of the flexion angle adjustment mechanism. The lateral edge can have a slight curvature (radius) that facilitates this engagement.

Figure 9A:
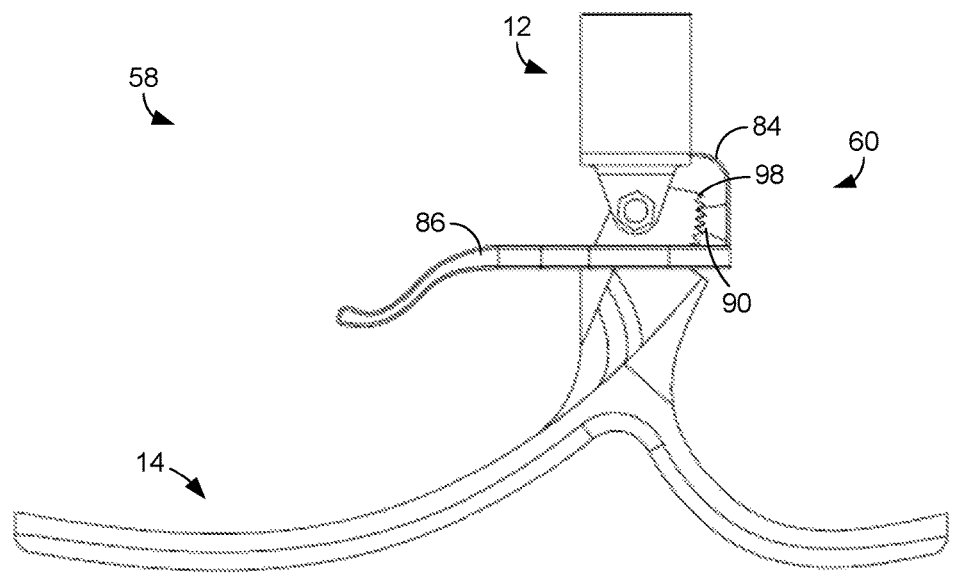
FIGS. 9A and 9B are side views of the lower-leg prosthesis of FIG. 6 illustrating adjustment of the flexion angle of the ankle of the prosthesis.
Figure 9B:
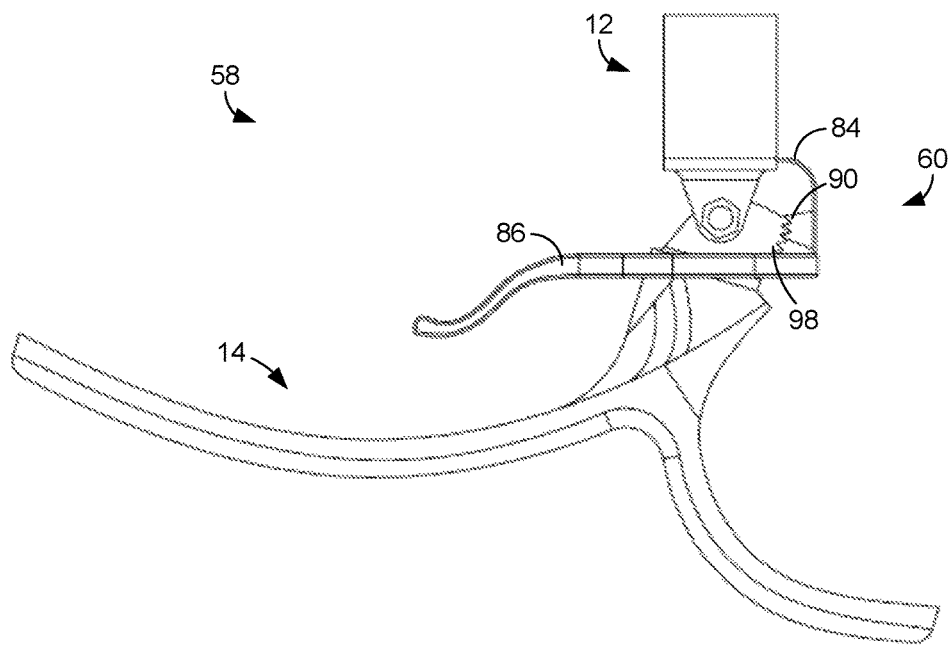

FIGS. 9A and 9B illustrate an example of use of the prosthetic ankle 60. Beginning with FIG. 9A, the ankle 60 is in a first configuration in which the teeth 90 of the lever 84 of the upper coupling member 62 are engaged with a first subset of teeth 98 of the 94 of the lower coupling member 66. This results in the ankle 60 having a particular angle of flexion (~0° in FIG. 9A). In FIG. 9B, the ankle 60 is in a second configuration that results when the user moves the lever 84 so as bend the compliant element 86 outward and disengage the teeth 90 from the teeth 98, and then re-engages the teeth in a different orientation. In such a case, the teeth 90 engage with a second subset of teeth 98. This results in the ankle 60 having a different angle of flexion (~17° in FIG. 9B). The total angle of adjustment for the ankle 60 as well as the number of discrete angular positions into which the ankle can be placed can be controlled by modifying the size (pitch) and/or number of teeth of the coupling members 62, 66.

Stress analysis was performed for the above-described embodiments in a SolidWorks® 2011 Simulation (Dassault Systems, Vélizy-Villacoublay, France). A static bearing load of 2,000 N was applied to each section of the ankle coupling members. The coupling members of the first embodiment (FIGS. 2-5) had a lower maximum von Mises stress of 79 megapascals (MPa). The upper and lower coupling members of the second embodiment (FIGS. 6-9) had maximum stresses of 93 and 99 MPa, respectively. These stresses fall well under the yield stress of tempered (T6) 6061 aluminum but are near the yield stress of the weaker tempered and annealed (T1 and O) aluminums with typical yield strengths of 241 and 97 MPa, respectively.

The above-described prosthetic ankle embodiments present potential solutions to the need for rugged, manually adjustable ankle prostheses. When properly adjusted, performance is expected to be similar to that of commercially available devices. In cases in which the ankles are made of aluminum alloys that resist corrosion and temperature embrittlement, the ankles are tolerant to cold, water, and ice. The disclosed embodiments enable the adjustment of ankle flexion for extended hill ascent and descent in amputees. The embodiments are also low in cost relative to microprocessor foot/ankle systems that may lack the durability to withstand rigorous environments and loads. Furthermore, the disclosed embodiments are completely mechanical in nature and therefore do not require battery recharging and are at lower risk of damage from being wet.

The invention claimed is:

1. An adjustable prosthetic ankle separate from a prosthetic foot, the prosthetic ankle comprising:
   a first coupling member including two mounting flanges;
   a second coupling member that couples with the first coupling member, the second coupling member including a mounting flange that is positioned between the two mounting flanges of the first coupling member, the mounting flange of the second coupling member having an edge that includes one or more teeth; and
   an adjustment lever that enables adjustment of an angle between the first and second coupling members, the adjustment lever including a compliant element that extends from the first coupling member and an elongated lever arm that extends from the compliant element, wherein one or more teeth extend from the adjustment lever and engage the one or more teeth of the second coupling member so as to fix the angle between the first and second coupling members;
   wherein movement of the elongated lever arm causes the compliant element to bend and the one or more teeth of the adjustment lever to disengage from the one or more teeth of the second coupling member to enable adjustment of the angle between the first and second coupling members.

2. The prosthetic ankle of claim 1, further comprising a threaded bolt that passes through aligned openings of the mounting flanges of the first and second coupling members and a threaded nut in which the threaded bolt is received.

3. The prosthetic ankle of claim 1, wherein the first coupling member comprises a base and wherein the adjustment lever extends from the base.

4. The prosthetic ankle of claim 3, wherein the two mounting flanges of the first coupling member extend from the base and taper as they extend.

5. The prosthetic ankle of claim 4, wherein the two mounting flanges of the first coupling member each form a generally triangular shape.

6. The prosthetic ankle of claim 1, wherein the one or more teeth of the second coupling member face outward from the prosthetic ankle and the one or more teeth of the first coupling member face inward into the prosthetic ankle.

7. The prosthetic ankle of claim 1, wherein the edge of the flange of the second coupling member is curved.

8. A lower-leg prosthesis comprising:
   a pylon;
   a prosthetic foot; and
   an adjustable prosthetic ankle separate from the pylon and the prosthetic foot that connects the foot to the pylon, the ankle comprising:
      a first coupling member including two mounting flanges,
      a second coupling member that couples with the first coupling member, the second coupling member including a mounting flange that is positioned between the two mounting flanges of the first coupling member, the mounting flange of the second coupling member having an edge that includes one or more teeth, and
      an adjustment lever that enables adjustment of an angle between the first and second coupling members, the adjustment lever including a compliant element that extends from the first coupling member and an elongated lever arm that extends from the compliant element, wherein one or more teeth extend from the adjustment lever and engage the one or more teeth of the second coupling member so as to fix the angle between the first and second coupling members;
      wherein movement of the elongated lever arm causes the compliant element to bend and the one or more teeth of the adjustment lever to disengage from the one or more teeth of the second coupling member to enable adjustment of the angle between the first and second coupling members.

9. The lower-leg prosthesis of claim 8, further comprising a threaded bolt that passes through aligned openings of the mounting flanges of the upper first and lower second coupling members and a threaded nut in which the threaded bolt is received.

10. The lower-leg prosthesis of claim 8, wherein the first coupling member comprises a base and wherein the adjustment lever extends from the base.

11. The lower-leg prosthesis of claim 10, wherein the two mounting flanges of the first coupling member extend from the base and taper as they extend.

12. The lower-leg prosthesis of claim 11, wherein the two mounting flanges of the first coupling member each form a generally triangular shape.

13. The lower-leg prosthesis of claim 8, wherein the one or more teeth of the second coupling member face outward from the prosthetic ankle and the one or more teeth of the first coupling member face inward into the prosthetic ankle.

14. The lower-leg prosthesis of claim 8, wherein the edge of the flange of the second coupling member is curved.

\* \* \* \* \*